United States Patent [19]

Holt et al.

[11] 4,194,149
[45] Mar. 18, 1980

[54] METHOD FOR GENERATING THE EDDY CURRENT SIGNATURE OF A FLAW IN A TUBE PROXIMATE A CONTIGUOUS MEMBER WHICH OBSCURES THE FLAW SIGNAL

[75] Inventors: Amos E. Holt; Allen E. Wehrmeister; Hubert L. Whaley, all of Lynchburg, Va.

[73] Assignee: The Babcock & Wilcox Company, New Orleans, La.

[21] Appl. No.: 860,811

[22] Filed: Dec. 15, 1977

[51] Int. Cl.² ............................................. G01R 33/12
[52] U.S. Cl. .................................. 324/220; 324/225; 324/238
[58] Field of Search ............................. 324/219–221, 324/225, 233, 238, 240, 241

[56] References Cited

U.S. PATENT DOCUMENTS

| 2,418,686 | 4/1947 | Zuschlag | 324/241 |
| 3,302,105 | 1/1967 | Libby et al. | 324/233 |

FOREIGN PATENT DOCUMENTS

| 2348787 | 4/1974 | Fed. Rep. of Germany . | |
| 283256 | 1/1928 | United Kingdom | 324/241 |

Primary Examiner—Robert J. Corcoran
Attorney, Agent, or Firm—John F. Luhrs; Robert J. Edwards

[57] ABSTRACT

A method for deriving the eddy current signature of a flaw in a tube proximate a contiguous member which is obscured in the composite signature of the flaw and contiguous member by subtracting from the composite signature a reference eddy current signature generated by a facsimile of the tube and contiguous member.

9 Claims, 10 Drawing Figures

SERVICE TUBE COMPOSITE — REFERENCE TUBE = FLAW
(REFERENCE SUPPORT PLATE SIGNAL)

METHOD FOR GENERATING THE EDDY CURRENT SIGNATURE OF A FLAW IN A TUBE PROXIMATE A CONTIGUOUS MEMBER WHICH OBSCURES THE FLAW SIGNAL

This invention relates to a method for determining the location and character of flaws in metal tubes. More particularly the invention relates to an in situ method for obtaining the eddy current signature of a flaw in a tube adjacent a contiguous member which obscures the flaw signature.

The invention finds application in the in situ eddy current testing for flaws in the tubes of heat exchangers such as used in fossil fuel and nuclear power plants. When placed in service the tubes in such heat exchangers are usually free from defects because of non-destructive testing and repair during and after manufacture. Over an extended period of usage flaws may appear in the tubes because of corrosion, erosion, stresses and the like. It is therefore essential that such tubes be periodically tested and the location and character of a flaw be determined so that a decision can be made as to the seriousness of the flaw and the corrective action to be taken.

Flaws in such tubes frequently occur at points of maximum stress adjacent support plates used to hold the tubes in desired configuration and adjacent tube sheets isolating the interior of the tubes from the exterior. It is therefore essential that if full advantage is to be taken of the eddy current method of detecting flaws in tubes, that the method be capable of generating the true signature of a flaw in the vicinity of a support plate or a tube sheet. As a tube sheet may, for purposes of this invention, be considered a special type of support plate, for convenience the generic term "support plate" will sometimes hereinafter be used.

Of critical importance is the need to locate and determine the character of flaws in the tubes in steam generators used in nuclear power producing units. Such steam generators may, for example, include upwards of sixteen thousand relatively thin walled small bore tubes, each having a length of sixty feet or more through which a coolant is circulated. The tubes are held in desired configuration by a plurality of support plates distributed along their length and by relatively thick tube sheets at their ends, which also seal the interior of each tube from its exterior. Ordinarily the tubes are made of an alloy, such as Inconel 600, whereas the support plates and tube sheets are made of carbon steel, thereby causing a material change in permeability and obscuring the eddy current signature of a flaw in the vicinity of such contiguous members.

The generation of eddy current signatures to locate flaws in what may be termed free standing tubes is well established in the art. Reference may be made, for example, to U.S. Pat. No. 3,302,105 which illustrates and describes the eddy current signatures of various types of tube defects. The teachings of this patent do not recognize, however, the obscuration of a defect signature proximate a contiguous member such as a support plate, there being illustrated only the characteristic "figure eight" eddy current signature generated by a sensor in scanning a sound tube proximate a contiguous member.

It is therefore an object of this invention to provide, inter alia, a method for obtaining the eddy current signature of a flaw in a tube proximate a contiguous member such as a support plate.

A further object of the invention is to provide a method whereby the degradation of such a tube over an extended period of usage can be monitored so that corrective action may be taken when such degradation becomes critical.

Still another object of the invention is to provide a method particularly adapted to the in situ eddy current scanning of tubes proximate contiguous support members in heat exchangers such as steam generataors and condensers found in nuclear and fossil fuel power producing units.

These and other objects will be apparent from the following description when considered in connection with the drawings, in which:

IN THE DRAWINGS

DETAILED DESCRIPTION

Figure 1:
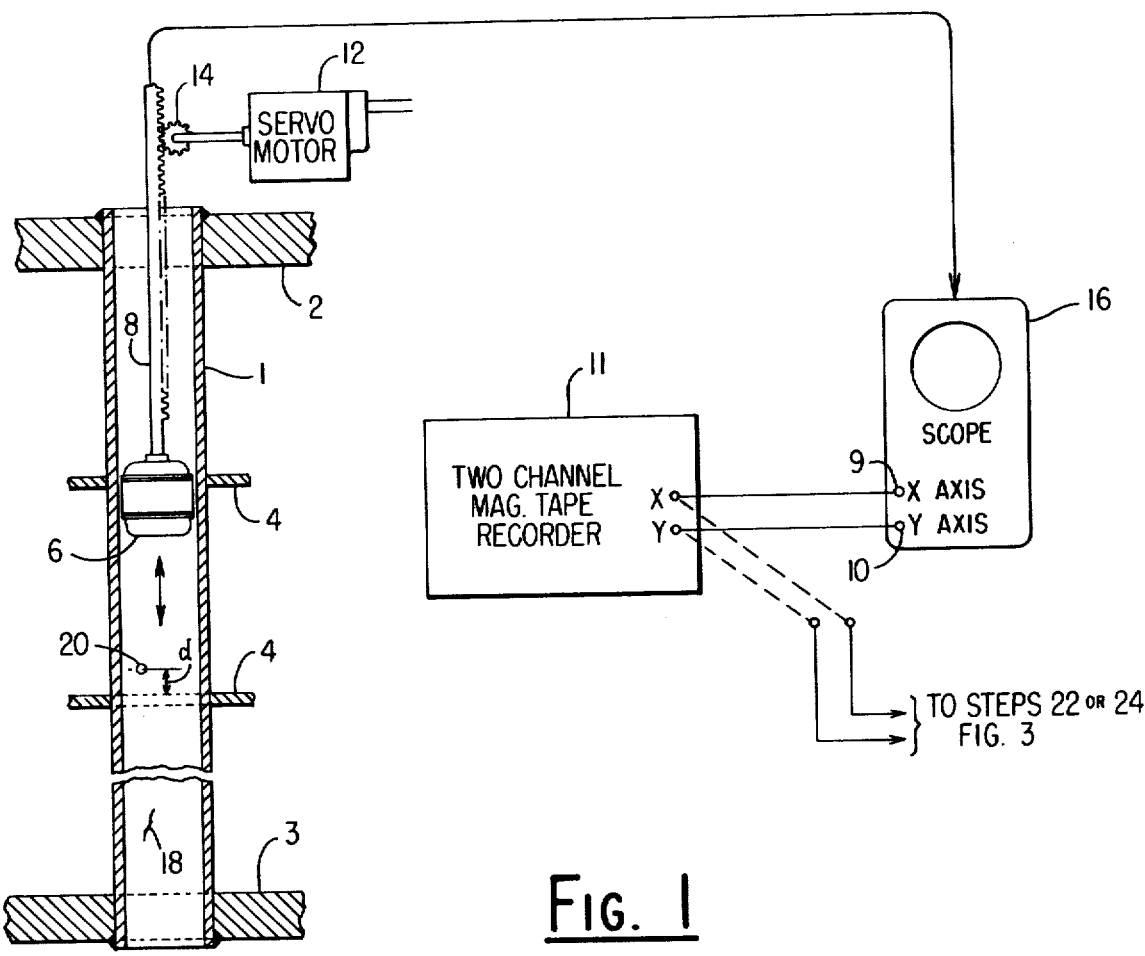
FIG. 1 is a schematic illustration of a typical apparatus for obtaining an eddy current signature.

Referring to the drawings, wherein like reference characters designate like or corresponding parts throughout the several views, there is shown in cross section a fragment of a tube 1, supported at its upper end by a tube sheet 2 and at its lower end by a tube sheet 3. The tube sheets 2 and 3 are welded to the tube 1 to isolate the interior of the tube from the exterior, so that, if the tube 1 comprises one of a plurality of tubes in a heat exchanger, a fluid circulated through the tube, which may be the coolant, for example, from a nuclear reactor, is isolated from the water and/or steam surrounding the exterior of the tube.

Distributed along the length of the tube are a plurality of support plates 4, holding the tube in desired position, or if one of a bundle of tubes, holding the tubes in desired configuration. The tube, or tubes, are not secured to the support plates by welding or the like, but pass through, with close tolerance, holes drilled or otherwise formed in the plates wich are also provided with passageways for the flow of steam and/or water along the exterior of the tubes. Ordinarily the tubes are made of an alloy, such as Inconel 600, whereas the support plates are made of carbon steel or a different alloy having a materially different electrical permeability than the tubes.

Shown within the tube 1 is a differential eddy current sensor 6, attached to a cable 8 for drawing the sensor through the tube 1 at a predetermined speed, usually in the order of one foot per second, by means of a constant speed servomotor 12 and drive pulley 14. Various arrangements are known for drawing the sensor through the tube, one such arrangement, particularly adapted to the eddy current scanning of tubes, being illustrated and described in copending Application Ser. No. 842,010 filed in the United States Patent and Trademark Office on Oct. 13, 1977. It is apparent that an absolute eddy current sensor may be used in place of the differential eddy current sensor 6 if desired.

In making a scan of the tube 1, the servomotor 12 is operated to position the sensor 6 to one end of the tube, or to a predetermined bench mark (not shown). The servomotor is then reversed and the sensor drawn through the tube at a predetermined constant speed. As illustrated in the aforesaid copending application a flexible cable is ordinarily employed to position the sensor 6, however, in FIG. 1 to indicate a positive drive connection, the cable 8 has been shown as including a rack engaging a pinion 14 driven by the servomotor 12.

Figures 2A, 2B, 2C:
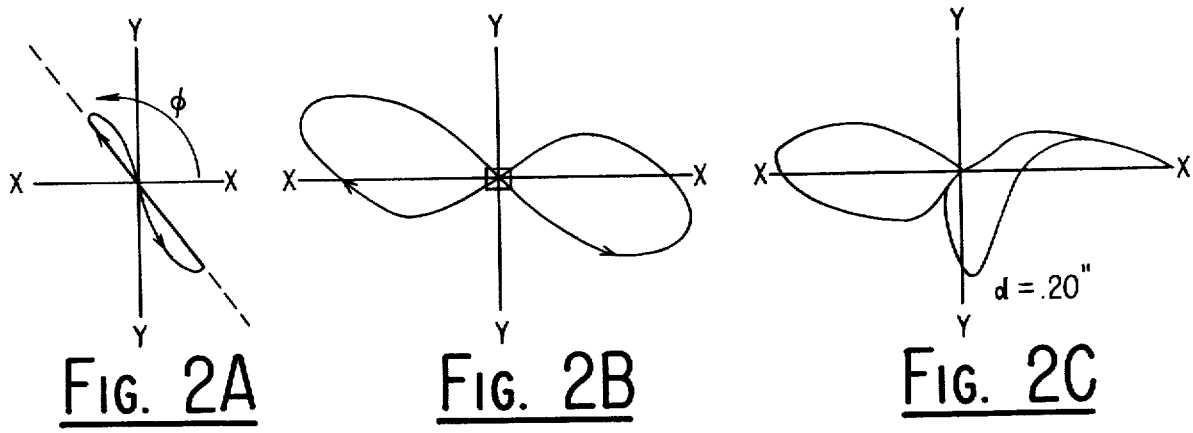
FIGS. 2A-2D are plots of various eddy current signatures.

The cable 8 also carries the electrical connections from the sensor 6 to an array of instruments used in the analysis of the eddy current signature, shown in FIG. 1 as comprising an eddy current tester such as a Zetec-/Automation Ind. EM 3300 Eddy Current Tester 16 and an Ampex/Zetec Model FM 755 Magnetic Tape Recorder 11. The signature appearing on the scope, as the sensor traverses the tube, will vary depending upon the character of the tube. Thus, following the usual circuit adjustments, as the sensor scans a sound portion of the tube, a minor horizontal deflection is obtained representative of the sensor wobble as it traverses the tube. The sensor, upon traversing a flaw 18, will generate a signal displayed on the scope as shown in FIG. 2A. From the characteristics of the display pattern and the phase angle $\phi$, the location, depth, and type of tube anomaly can be determined.

In FIG. 2B is shown a typical fat, two lobed signal generated by the sensor, as displayed on the scope, in traversing a support plate.

Figure 2D:
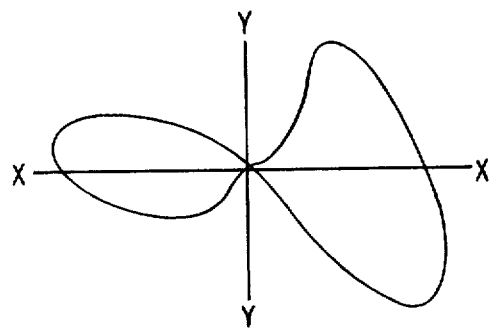

This signal may be termed a reference support plate signal and is generated due to the high permeability of the ferretic steel of which a support plate is made. If, however, a defect is present in the tube adjacent a contiguous member, such as a support plate, the normal support plate signal will be distorted. In this case a composite signal (flaw plus support plate) is obtained. Typical of the composite signal, as displayed on the scope, as shown in FIG. 2C, is that produced by a flaw 20 in the tube 0.20 inches above the top endge of a support plate 4. If the flaw 20 is, however, so located that its lower edge is aligned with the top surface of the support plate 4, a composite signature, as shown in FIG. 2D, is produced. It is apparent that if the support plate signal, as shown in FIG. 2B, is distorted because of a tube anomaly, conventional eddy current analysis is inadequate on which to base a decision as to whether or not a disturbing influence is due to a harmful or harmless condition in the tube. It has been found, in scanning a typical tube, that the region of influence on the eddy current signature includes not only the contiguous member, but may extend on the order of one half inch in either direction beyond the contiguous member. In addition, the shape of the distorted signal (composite) changes continously with small changes in the relative positions of the flaw and support plate.

Figure 3:
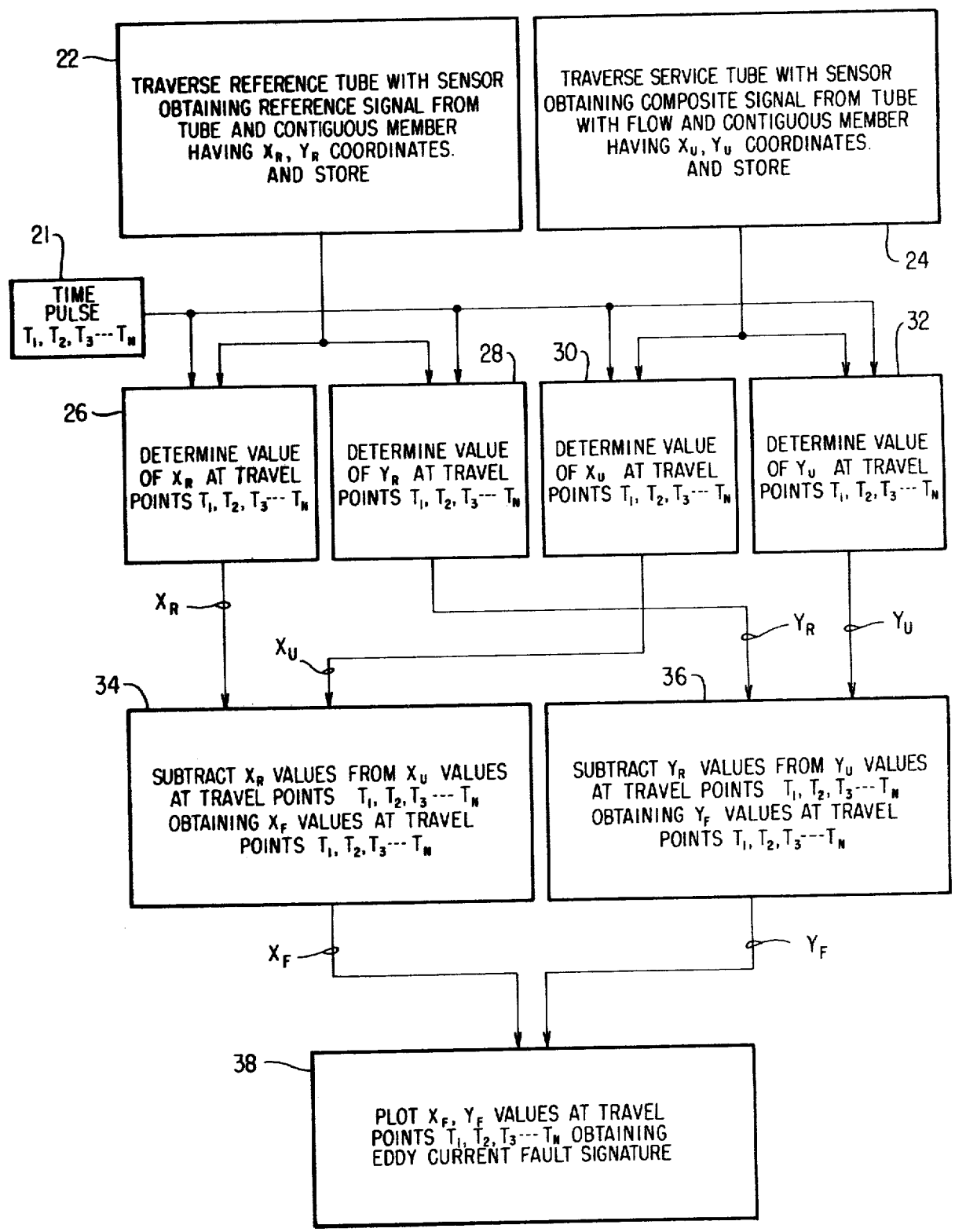
FIG. 3 is a block diagram of the steps employed in the method of obtaining the eddy current signature of a flaw in a tube proximate a contiguous member.

Referring to FIG. 3 there is shown, in block form, the steps of this novel method by which the eddy current signature of a flaw in a tube proximate a contiguous member may be determined. In this method, as shown in block 22, the $X_R$, $Y_R$, (horizontal and vertical) coordinates of a reference eddy current signal, available at terminals 9 and 10, produced by scanning a reference or facsimile tube and contiguous member is obtained and stored in a suitable storage device, such as the magnetic tape recorder 11. These records of the $X_R$, $Y_R$ coordinates of the reference eddy current signal may be retained, if required, more or less permanently, to be compared periodically against the $X_U$, $Y_U$ coordinates of the service tube and contiguous member eddy current signal.

By reference or facsimile tube and contiguous member is meant an arrangement of a sound tube and contiguous member similar to that of the unknown or service tube and contiguous member which is scanned to determine the presence or absence of flaws. The reference tube and contiguous member may be adjacent to or remote from the service tube and contiguous member. It may consist only of that portion of a tube and contiguous member of critical importance. It may comprise a portion of the service tube, known to be flawless, proximate a contiguous member by exhibiting a trace having the characteristics heretofore described and illustrated in FIG. 2B.

As shown in block 24 the service tube is scanned and the $X_U$, $Y_U$ coordinates of the eddy current signal stored in a magnetic tape recorder similar to the magnetic tape recorder 11. It is immaterial whether or not the scan of the reference tube and contiguous member is made before or after the scan of the service tube and contiguous member. Preferably the scans are made at identical speeds and the recorders also are operated at identical speeds.

As shown in blocks 26, 28, 30 and 32 the values of the $X_R$, $Y_R$ and $X_U$, $Y_U$ components of the eddy current signal for the reference and service tubes at travel points $T_1$, $T_2$, $T_3$—$T_N$ are determined. The travel points $T_1$, $T_2$, $T_3$—$T_N$ may be, as shown, identified by a clock 21, generating a signal pulse at each predetermined increment of time. Signal pulses may also be obtained directly from any suitable means operatively connected to the servomotor 12 in view of the positive drive connection between the servomotor and cable 8.

As shown in block 34 the $X_R$ values at the identified travel points are then subtracted from the corresponding $X_U$ values, the resultant being the $X_F$ L(X component values of a flaw signal) at the identified travel points. Similarly, corresponding values of the $Y_F$ (Y component values of a flaw signal) are obtained as shown in block 36.

As shown in block 38 the eddy current signature of a flaw is then generated from a plot of the corresponding $X_F$, $Y_F$ components at the identified travel points.

Figures 4A, 4B, 4C:
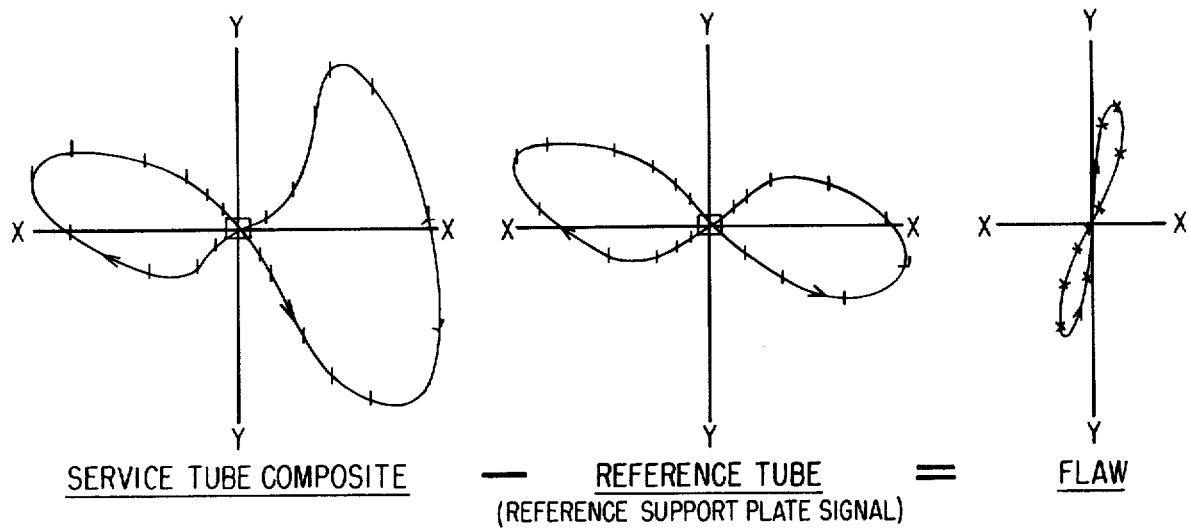
FIG. 4A-4C illustrate graphically the steps set forth in FIG. 3.

The method is graphically illustrated in FIGS. 4A–4C. FIG. 4A shows the composite eddy current signal of a service tube having a flaw proximate a contiguous member which has been plotted from the $X_U$, $Y_U$ components at identified travel points as determined in steps 30, 32. FIG. 4B shows the reference support plate signature from the reference or facsimile tube adjacent a contiguous member which has been plotted from the $X_R$, $Y_R$ components at the identified travel points. FIG. 4C shows the eddy current flaw signature derived by subtracting from the service tube composite signal, the reference signal at the identified travel points.

In FIG. 4A the vector of the composite signal at travel points $T_1$, $T_2$, $T_3$—$T_N$ can be determined by means of the $X_U$, $Y_U$ coordinates at these travel points. Similarly, the vector of the reference signal at travel points $T_1$, $T_2$, $T_3$—$T_N$ can be determined. The flaw signature can then be constructed by the vector subtraction of the reference vectors from the corresponding composite vectors, to produce the resultant flaw vectors at travel points $T_1, T_2, T_3\text{---}T_N$.

From the foregoing it will be apparent that the method herein disclosed can be embodied in various types of computing circuits, analog or digital, or a combination of analog and digital. For example, by the use of a mini computer, the reference and composite signals may be digitized and stored in the memory and the described method performed to produce the output signals $X_F, Y_F$ in digital form for plotting.

Figure 5:
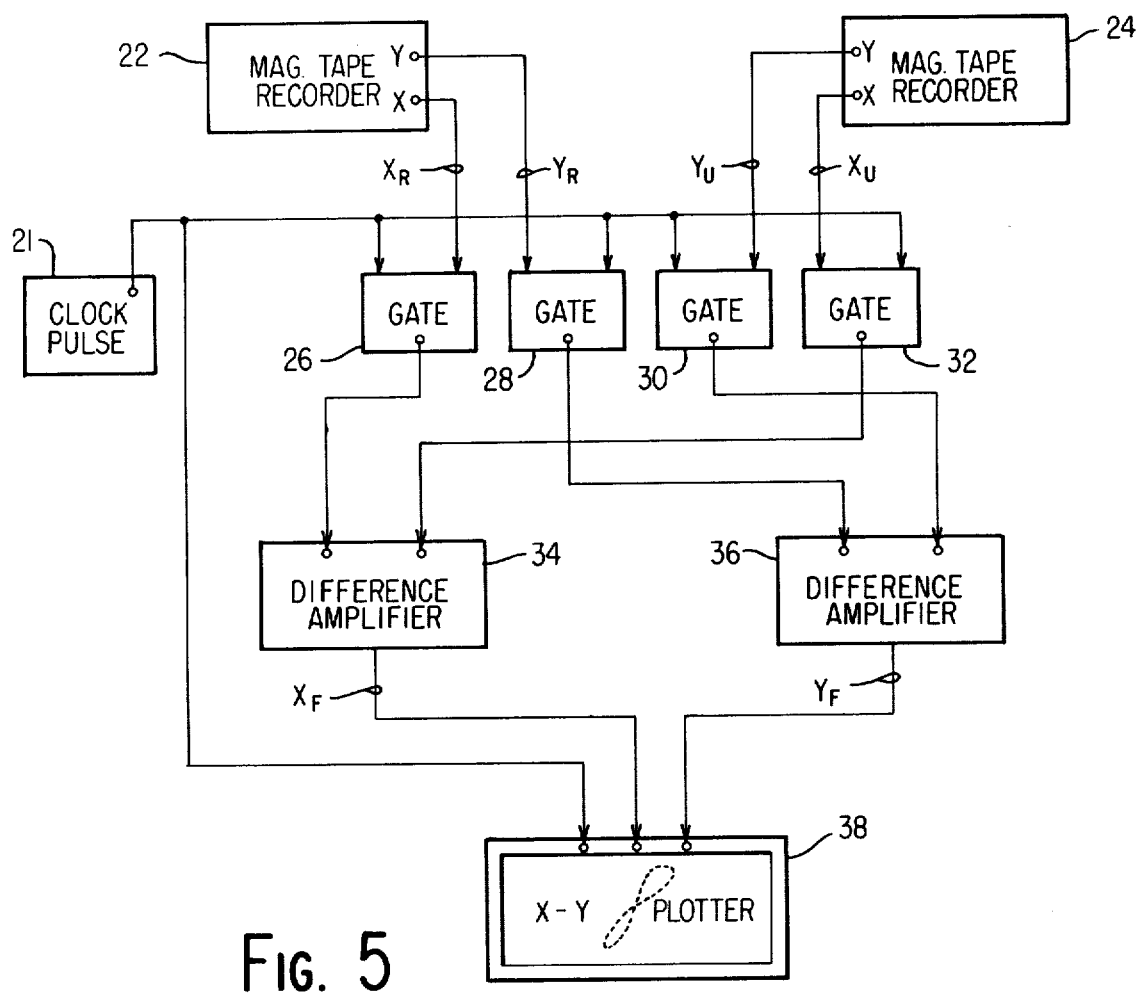
FIG. 5 is an elementary diagram of an analog computing circuit for plotting the eddy current signature of a flaw in a tube proximate a contiguous member in accordance with the method set forth in FIG. 3.

In FIG. 5 there is shown a one line elementary diagram of an analog circuit embodying the method herein disclosed. In accordance with steps 22, 24 of the method as outlined in FIG. 3, the $X_R, Y_R$ coordinates of the reference signal and the $X_U, Y_U$ coordinates of the composite signal are recorded and stored in magnetic tape recorders 22, 24. These tapes are then played back in synchronism and in phase. By means of gates 26,32 the values of $X_R, X_U$ input to a difference amplifier 34 at predetermined sensor travel points as inferentially obtained from pulses generated in clock 21. Similarly, by means of gates 28, 30 the values of $Y_R, Y_U$ input to difference amplifier 36 at the predetermined sensor travel points. Difference amplifier 34 generates the output signal $X_F$, and difference amplifier 36 generates the output signal $Y_F$. These two signals are transmitted to an X-Y plotter 38 along with the pulses from clock 21 in which a plot of the eddy current flaw signature is generated and recorded.

The tape recorders 22, 24 may be played back in synchronism and in phase from corresponding bench marks at a selected speed which may be the same as or different from the speed at which the output signals from the eddy current sensor are recorded. The clock pulses generated in unit 21, inferentially proportional to increments of sensor travel, may be adjusted to any desired frequency as required to accurately plot the eddy current signature of a flaw.

We claim:

1. The method of generating the eddy current signature of a flaw in a tube proximate a contiguous member which obscures the flaw signature comprising, traversing a reference tube with an eddy current sensor proximate a similar contiguous member to obtain a reference eddy current signature of the first named contiguous member, performing a duplicate traverse of the first named tube to obtain a composite eddy current signature of the flaw and contiguous member, and generating the eddy current signature of the flaw by comparing the composite signature with the reference signature "wherein the step of comparing the composite signature with the reference signature to generate the flaw signature comprises, determining the vector of the reference signature at selected travel points of the sensor, determining the vector of the composite signature at the selected travel points and constructing the flaw signature from the resultant vectors derived by the vector subtraction of the reference vector from the composite vector at the selected travel points".

2. The method as set forth in claim 1 wherein the vectors of the composite and reference eddy current signatures are derived from the X, Y (horizontal and vertical) coordinates of the respective eddy current signals at each of the selected travel points.

3. The method as set forth in claim 2 wherein the resultant vectors of the flaw signature are derived from the X, Y coordinates computed by substracting from X component of the composite eddy current signal the X component of the reference eddy current signal, and subtracting from the Y component of the composite eddy current signal the Y component of the reference signal at each of the selected travel points.

4. The method of generating the eddy current signature of a flaw in a tube proximate a contiguous member which obscures the flaw signature comprising, traversing a reference tube with an eddy current sensor proximate a contiguous member to obtain a reference eddy current signature of the contiguous member, performing a duplicate traverse of the first named tube to obtain a composite eddy current signature of the flaw and contiguous member, determining the $X_R, Y_R$ coordinates of the reference eddy current signature at selected sensor travel points, determining the $X_U, Y_U$ coordinates of the composite eddy current signal at the selected sensor travel points, subtracting the $X_R$ component from the $X_U$ component and the $Y_R$ component from the $Y_U$ component at the selected sensor travel points to generate the $X_F, Y_F$ coordinates of the flaw signature at the selected travel points and plotting the flaw signature from the $X_F, Y_F$ coordinates.

5. The method as set forth in claim 4 wherein the traverses of the eddy current sensor are made from at least 0.5 inches from one face of the contiguous member to at least 0.5 inches beyond the opposite face of the contiguous member.

6. The method as set forth in claim 4 wherein the traverses of the eddy current sensor are made at a speed in the order of twelve inches per second.

7. The method as set forth in claim 4 wherein selected time increments bearing a known ratio to increments of sensor travel are utilized to establish the selected sensor travel points.

8. The method as set forth in claim 4 further including the steps of recording the $X_R, Y_R$ coordinates and the $X_U, Y_U$ coordinates in phase and in synchronism on separate magnetic tapes and playing the tapes back in phase and in synchronism to generate output signals corresponding to the $X_R, Y_R$ and $X_U, Y_U$ coordinates.

9. The method as set forth in claim 8 further including the step of automatically plotting the eddy current signature on an X-Y plotter receiving the $X_F$ and $Y_F$ coordinates of the eddy current signature at the selected sensor travel points.

* * * * *